(12) United States Patent
Peterson et al.

(10) Patent No.: US 10,085,747 B2
(45) Date of Patent: Oct. 2, 2018

(54) SURGICAL FASTENING INSTRUMENT

(71) Applicant: Incisive Surgical, Inc., Plymouth, MN (US)

(72) Inventors: James A. Peterson, Edina, MN (US); David B. Herridge, Mendota Heights, MN (US); Christopher J. Sperry, Plymouth, MN (US); Chad D. Naegeli, Andover, MN (US)

(73) Assignee: Incisive Surgical, Inc., Plymouth, MN (US)

( * ) Notice: Subject to any disclaimer, the term of this patent is extended or adjusted under 35 U.S.C. 154(b) by 341 days.

(21) Appl. No.: 14/851,308

(22) Filed: Sep. 11, 2015

(65) Prior Publication Data

US 2017/0071602 A1 Mar. 16, 2017

(51) Int. Cl.
 *A61B 17/10* (2006.01)
 *A61B 17/068* (2006.01)
 (Continued)

(52) U.S. Cl.
 CPC ...... *A61B 17/0682* (2013.01); *A61B 17/0644* (2013.01); *A61B 17/02* (2013.01);
 (Continued)

(58) Field of Classification Search
 CPC . A61B 17/02; A61B 17/0644; A61B 17/0682; A61B 17/282; A61B 17/30; A61B 2017/081
 See application file for complete search history.

(56) References Cited

U.S. PATENT DOCUMENTS

| 718,649 A | 1/1903 | Morehouse |
| 2,283,814 A | 5/1942 | LaPlace |

(Continued)

FOREIGN PATENT DOCUMENTS

| EP | 1323384 | 7/2003 |
| EP | 0657139 | 12/2003 |

(Continued)

OTHER PUBLICATIONS

Application and File history for U.S. Appl. No. 14/262,071, filed Apr. 25, 2014. Inventors: Peterson et al.

(Continued)

*Primary Examiner* — Ashley Fishback
(74) *Attorney, Agent, or Firm* — Patterson Thuente Pedersen, P.A.

(57) ABSTRACT

A surgical fastening apparatus and related methods for fastening skin tissue so as to avoid piercing the epidermis with resultant percutaneous penetration when intending placement of surgical fasteners within a dermal layer on opposed sides of a skin wound. The apparatus includes a device body having a head portion for positioning between first and second sides of the wound, wherein the head portion includes a deflector shelf that physically prevents epidermal tissue from entering a capture zone defined on the head portion through which a penetrator assembly and fastener are advanced into the dermal layer. By ensuring that the epidermal tissue is not placed within the piercing zone, the potential for inadvertent piercing and percutaneous placement of the surgical fastener though the external skin surface is avoided.

15 Claims, 13 Drawing Sheets

(51) Int. Cl.
  *A61B 17/064*  (2006.01)
  *A61B 17/02*   (2006.01)
  *A61B 17/28*   (2006.01)
  *A61B 17/30*   (2006.01)
  *A61B 17/08*   (2006.01)
  *A61B 90/00*   (2016.01)

(52) U.S. Cl.
  CPC ............ *A61B 17/282* (2013.01); *A61B 17/30* (2013.01); *A61B 2017/081* (2013.01); *A61B 2090/0807* (2016.02)

(56) References Cited

U.S. PATENT DOCUMENTS

| | | |
|---|---|---|
| 2,344,071 A | 3/1944 | Wilson et al. |
| 2,351,608 A | 6/1944 | Greenwood |
| 2,439,383 A | 4/1948 | Erickson |
| 2,526,902 A | 10/1950 | Rublee |
| 2,881,762 A | 4/1959 | Lowrie |
| 2,959,172 A | 11/1960 | Held |
| 3,074,409 A | 1/1963 | Bielz |
| 3,082,426 A | 3/1963 | Miles |
| 3,123,077 A | 3/1964 | Alcamo |
| 3,297,033 A | 1/1967 | Schmitt et al. |
| 3,344,790 A | 10/1967 | Dorner |
| 3,570,497 A | 3/1971 | Lemole |
| 3,601,302 A | 8/1971 | Potekhina et al. |
| 3,636,956 A | 1/1972 | Schneider |
| 3,638,654 A | 2/1972 | Akuba |
| 3,643,851 A | 2/1972 | Green et al. |
| 3,716,058 A | 2/1973 | Tanner, Jr. |
| 3,757,629 A | 9/1973 | Schneider |
| 3,792,010 A | 2/1974 | Wasserman et al. |
| 3,855,688 A | 12/1974 | Knohl |
| 3,858,783 A | 1/1975 | Kapitanov et al. |
| 4,014,492 A | 3/1977 | Rothfuss |
| 4,027,676 A | 6/1977 | Mattei |
| 4,047,533 A | 9/1977 | Perciaccante et al. |
| 4,162,678 A | 7/1979 | Fedotov et al. |
| 4,164,225 A | 8/1979 | Johnson et al. |
| 4,204,541 A | 5/1980 | Kapitanov |
| 4,217,902 A | 8/1980 | March |
| 4,259,959 A | 4/1981 | Walker |
| 4,261,244 A | 4/1981 | Becht et al. |
| 4,317,451 A | 3/1982 | Cerwin et al. |
| 4,345,601 A | 8/1982 | Fukuda |
| 4,354,628 A | 10/1982 | Green |
| 4,396,139 A | 8/1983 | Hall et al. |
| 4,399,810 A | 8/1983 | Samuels et al. |
| 4,407,286 A | 10/1983 | Noiles et al. |
| 4,410,125 A | 10/1983 | Noiles et al. |
| D271,418 S | 11/1983 | Campbell et al. |
| 4,428,376 A | 1/1984 | Mericle |
| 4,430,998 A | 2/1984 | Harvey et al. |
| 4,434,796 A | 3/1984 | Karapetian et al. |
| 4,440,171 A | 4/1984 | Nomoto et al. |
| 4,454,875 A | 6/1984 | Pratt et al. |
| 4,467,805 A | 8/1984 | Fukuda |
| 4,484,580 A | 11/1984 | Nomoto et al. |
| 4,485,816 A | 12/1984 | Krumme |
| 4,485,953 A | 12/1984 | Rothfuss |
| 4,493,322 A | 1/1985 | Becht |
| 4,505,273 A | 3/1985 | Braun et al. |
| 4,506,669 A | 3/1985 | Blake, III |
| D278,656 S | 4/1985 | Green et al. |
| 4,508,253 A | 4/1985 | Green |
| 4,513,746 A | 4/1985 | Aranyi et al. |
| 4,526,173 A | 7/1985 | Sheehan |
| 4,526,174 A | 7/1985 | Froehlich |
| 4,534,352 A | 8/1985 | Korthoff |
| 4,535,772 A | 8/1985 | Sheehan |
| 4,539,990 A | 9/1985 | Stivala |
| 4,548,202 A | 10/1985 | Duncan |
| 4,557,265 A | 12/1985 | Andersson |
| 4,566,620 A | 1/1986 | Green et al. |
| 4,568,009 A | 2/1986 | Green |
| 4,570,623 A | 2/1986 | Ellison et al. |
| 4,573,622 A | 3/1986 | Green et al. |
| 4,583,670 A | 4/1986 | Alvarado |
| 4,592,498 A | 6/1986 | Braun et al. |
| 4,593,843 A | 6/1986 | Saravis |
| 4,596,249 A | 6/1986 | Freda et al. |
| 4,596,350 A | 6/1986 | Smith et al. |
| 4,603,693 A | 8/1986 | Conta et al. |
| 4,607,638 A | 8/1986 | Crainich |
| 4,610,251 A | 9/1986 | Kumar |
| 4,618,086 A | 10/1986 | Li et al. |
| 4,619,262 A | 10/1986 | Taylor |
| D287,630 S | 1/1987 | Sharkany et al. |
| 4,637,380 A | 1/1987 | Orejola |
| 4,646,741 A | 3/1987 | Smith |
| 4,655,222 A | 4/1987 | Florez et al. |
| 4,665,916 A | 5/1987 | Green |
| 4,671,279 A | 6/1987 | Hill |
| 4,676,245 A | 6/1987 | Fukuda |
| 4,696,300 A | 9/1987 | Anderson |
| 4,719,917 A | 1/1988 | Barrows et al. |
| 4,724,840 A | 2/1988 | McVay et al. |
| 4,728,020 A | 3/1988 | Green et al. |
| 4,741,337 A | 5/1988 | Smith et al. |
| 4,752,024 A | 6/1988 | Green et al. |
| 4,753,636 A | 6/1988 | Free |
| 4,762,260 A | 8/1988 | Richards et al. |
| 4,776,506 A | 10/1988 | Green |
| 4,789,090 A | 12/1988 | Blake, III |
| 4,799,483 A | 1/1989 | Kraff |
| 4,802,478 A | 2/1989 | Powell |
| 4,809,695 A | 3/1989 | Gwathmey et al. |
| 4,869,414 A | 9/1989 | Green et al. |
| 4,873,976 A | 10/1989 | Schreiber |
| 4,887,601 A | 12/1989 | Richards |
| 4,887,756 A | 12/1989 | Puchy |
| 4,895,148 A | 1/1990 | Bays et al. |
| 4,899,745 A | 2/1990 | Laboureau et al. |
| 4,915,100 A | 4/1990 | Green |
| 4,924,866 A | 5/1990 | Yoon |
| 4,932,960 A | 6/1990 | Green et al. |
| 4,938,408 A | 7/1990 | Bedi et al. |
| 4,955,898 A | 9/1990 | Matsutani et al. |
| 4,969,591 A | 11/1990 | Richards et al. |
| 4,976,686 A | 12/1990 | Ball et al. |
| 4,976,715 A | 12/1990 | Bays et al. |
| 4,979,954 A | 12/1990 | Gwathmey et al. |
| 4,981,149 A | 1/1991 | Yoon et al. |
| 4,994,073 A | 2/1991 | Green |
| 5,002,562 A | 3/1991 | Oberlander |
| 5,002,563 A | 3/1991 | Pyka |
| 5,007,921 A | 4/1991 | Brown |
| 5,015,252 A | 5/1991 | Jones |
| 5,026,390 A | 6/1991 | Brown |
| 5,035,692 A | 7/1991 | Lyon et al. |
| 5,041,128 A | 8/1991 | Korthoff |
| 5,044,540 A | 9/1991 | Dulebohn |
| 5,047,047 A | 9/1991 | Yoon |
| 5,053,047 A | 10/1991 | Yoon |
| 5,058,315 A | 10/1991 | Wagner |
| 5,062,563 A | 11/1991 | Green et al. |
| 5,067,959 A | 11/1991 | Korthoff |
| 5,078,731 A | 1/1992 | Hayhurst |
| 5,080,665 A | 1/1992 | Jarrett et al. |
| 5,084,063 A | 1/1992 | Korthoff |
| 5,089,009 A | 2/1992 | Green |
| 5,089,010 A | 2/1992 | Korthoff |
| 5,089,011 A | 2/1992 | Korthoff |
| 5,104,394 A | 4/1992 | Knoepfler |
| 5,108,422 A | 4/1992 | Green et al. |
| 5,123,913 A | 6/1992 | Wilk et al. |
| 5,129,570 A | 7/1992 | Schulze et al. |
| 5,133,738 A | 7/1992 | Korthoff et al. |
| 5,139,514 A | 8/1992 | Korthoff et al. |
| 5,156,315 A | 10/1992 | Green et al. |
| 5,156,609 A | 10/1992 | Nakao et al. |
| 5,156,615 A | 10/1992 | Korthuff et al. |
| 5,158,566 A | 10/1992 | Pianetti |

(56) References Cited

U.S. PATENT DOCUMENTS

| | | |
|---|---|---|
| 5,158,567 A | 10/1992 | Green |
| 5,160,339 A | 11/1992 | Chen et al. |
| 5,176,306 A | 1/1993 | Heimerl et al. |
| 5,179,964 A | 1/1993 | Cook |
| 5,211,644 A | 5/1993 | VanBeek et al. |
| 5,211,722 A | 5/1993 | Wagner |
| 5,222,976 A | 6/1993 | Yoon |
| 5,226,912 A | 7/1993 | Kaplan et al. |
| 5,236,440 A | 8/1993 | Hlavacek |
| 5,242,457 A | 9/1993 | Akopov et al. |
| 5,257,713 A | 11/1993 | Green et al. |
| 5,258,009 A | 11/1993 | Conners |
| 5,258,010 A | 11/1993 | Green et al. |
| 5,258,012 A | 11/1993 | Luscombe et al. |
| 5,259,845 A | 11/1993 | Korthoff |
| 5,263,973 A | 11/1993 | Cook |
| 5,269,783 A | 12/1993 | Sander |
| 5,269,792 A | 12/1993 | Kovac et al. |
| 5,275,166 A | 1/1994 | Vaitekunas et al. |
| 5,282,807 A | 2/1994 | Knoepfler |
| 5,285,944 A | 2/1994 | Green et al. |
| 5,292,326 A | 3/1994 | Green et al. |
| 5,293,881 A | 3/1994 | Green et al. |
| 5,297,714 A | 3/1994 | Kramer |
| 5,304,204 A | 4/1994 | Bregen |
| 5,306,281 A | 4/1994 | Beurrier |
| 5,324,307 A | 6/1994 | Jarrett et al. |
| 5,330,503 A | 7/1994 | Yoon |
| 5,333,772 A | 8/1994 | Rothfuss et al. |
| 5,337,937 A | 8/1994 | Remiszewski et al. |
| 5,342,376 A | 8/1994 | Ruff |
| 5,350,400 A | 9/1994 | Esposito et al. |
| 5,356,424 A | 10/1994 | Buzerak et al. |
| 5,364,003 A | 11/1994 | Williamson, IV |
| 5,366,134 A | 11/1994 | Green et al. |
| 5,389,102 A | 2/1995 | Green et al. |
| 5,392,979 A | 2/1995 | Green et al. |
| 5,398,861 A | 3/1995 | Green |
| D357,316 S | 4/1995 | Green et al. |
| 5,413,584 A | 5/1995 | Schulze |
| 5,415,334 A | 5/1995 | Williamson, IV et al. |
| 5,417,361 A | 5/1995 | Williamson, IV |
| 5,423,856 A | 6/1995 | Green |
| 5,423,857 A | 6/1995 | Rosenman et al. |
| 5,425,489 A | 6/1995 | Schichman et al. |
| 5,425,747 A | 6/1995 | Brotz |
| 5,456,400 A | 10/1995 | Shichman et al. |
| 5,456,401 A | 10/1995 | Green et al. |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Greer et al. |
| 5,489,058 A | 2/1996 | Plyley et al. |
| 5,489,287 A | 2/1996 | Green et al. |
| 5,499,990 A | 3/1996 | Schulken et al. |
| 5,505,363 A | 4/1996 | Green et al. |
| 5,509,596 A | 4/1996 | Green et al. |
| 5,514,149 A | 5/1996 | Green et al. |
| 5,542,594 A | 8/1996 | McKean et al. |
| 5,544,802 A | 8/1996 | Crainich |
| 5,549,619 A | 8/1996 | Peters et al. |
| 5,551,622 A | 9/1996 | Yoon |
| 5,558,266 A | 9/1996 | Green et al. |
| 5,562,241 A | 10/1996 | Knodel et al. |
| 5,571,285 A | 11/1996 | Chow et al. |
| 5,573,541 A | 11/1996 | Green et al. |
| 5,573,542 A | 11/1996 | Stevens |
| 5,575,800 A | 11/1996 | Gordon |
| 5,579,978 A | 12/1996 | Green et al. |
| 5,584,859 A | 12/1996 | Brotz |
| 5,591,178 A | 1/1997 | Green et al. |
| 5,593,423 A | 1/1997 | Person et al. |
| 5,618,311 A | 4/1997 | Gryskiewicz |
| 5,645,567 A | 7/1997 | Crainich |
| 5,655,698 A | 8/1997 | Yoon |
| 5,658,312 A | 8/1997 | Green et al. |
| 5,662,258 A | 9/1997 | Knodel et al. |
| 5,662,655 A | 9/1997 | Laboureau et al. |
| 5,667,527 A | 9/1997 | Cook |
| 5,706,997 A | 1/1998 | Green et al. |
| 5,722,981 A | 3/1998 | Stevens |
| 5,725,538 A | 3/1998 | Green et al. |
| 5,725,554 A | 3/1998 | Simon et al. |
| 5,728,108 A | 3/1998 | Griffiths et al. |
| 5,741,278 A | 4/1998 | Stevens |
| 5,782,844 A | 7/1998 | Yoon et al. |
| 5,792,152 A | 8/1998 | Klein et al. |
| 5,794,834 A | 8/1998 | Hamblin et al. |
| 5,816,471 A | 10/1998 | Plyley et al. |
| 5,829,662 A | 11/1998 | Allen et al. |
| 5,843,084 A | 12/1998 | Hart et al. |
| 5,871,135 A | 2/1999 | Williamson, IV et al. |
| 5,878,937 A | 3/1999 | Green et al. |
| 5,902,311 A | 5/1999 | Andreas et al. |
| 5,902,319 A | 5/1999 | Daley |
| 5,908,149 A | 6/1999 | Welch et al. |
| 5,908,427 A | 6/1999 | McKean et al. |
| 5,921,994 A | 7/1999 | Andreas et al. |
| 5,947,999 A | 9/1999 | Groiso |
| 5,964,774 A | 10/1999 | McKean et al. |
| 5,976,160 A | 11/1999 | Crainich |
| 5,984,949 A | 11/1999 | Levin |
| 5,993,476 A | 11/1999 | Groiso |
| 6,036,699 A | 3/2000 | Andreas et al. |
| 6,036,701 A | 3/2000 | Rosenman |
| 6,039,753 A | 3/2000 | Meislin |
| 6,045,560 A | 4/2000 | McKean et al. |
| 6,083,242 A | 7/2000 | Cook |
| 6,090,131 A | 7/2000 | Daley |
| 6,120,526 A | 9/2000 | Daley |
| 6,131,789 A | 10/2000 | Schulze et al. |
| 6,136,010 A | 10/2000 | Modesitt et al. |
| 6,149,658 A | 11/2000 | Gardiner et al. |
| 6,159,224 A | 12/2000 | Yoon |
| 6,241,747 B1 | 6/2001 | Ruff |
| 6,250,532 B1 | 6/2001 | Green et al. |
| 6,270,517 B1 | 8/2001 | Brotz |
| 6,325,805 B1 | 12/2001 | Ogilvie et al. |
| 6,387,104 B1 | 5/2002 | Pugsley, Jr. et al. |
| 6,387,113 B1 | 5/2002 | Hawkins et al. |
| 6,409,743 B1 | 6/2002 | Fenton, Jr. |
| 6,423,088 B1 | 7/2002 | Fenton, Jr. |
| 6,443,962 B1 | 9/2002 | Gaber |
| 6,514,263 B1 | 2/2003 | Stefanchik et al. |
| 6,530,933 B1 | 3/2003 | Yeung et al. |
| 6,599,310 B2 | 7/2003 | Leung et al. |
| 6,601,748 B1 | 8/2003 | Fung et al. |
| 6,619,529 B2 | 9/2003 | Green et al. |
| 6,626,916 B1 | 9/2003 | Yeung et al. |
| 6,629,988 B2 | 10/2003 | Weadock |
| 6,638,297 B1 | 10/2003 | Huitema |
| 6,652,538 B2 | 11/2003 | Kayan et al. |
| 6,666,872 B2 | 12/2003 | Barreiro et al. |
| 6,692,499 B2 | 2/2004 | Törmälä |
| 6,726,705 B2 | 4/2004 | Peterson et al. |
| 6,767,356 B2 | 7/2004 | Kanner et al. |
| 6,773,437 B2 | 8/2004 | Ogilvie et al. |
| 7,112,214 B2 | 9/2006 | Peterson et al. |
| D532,107 S | 11/2006 | Peterson et al. |
| 7,547,315 B2 | 6/2009 | Peterson et al. |
| 7,682,372 B2 | 3/2010 | Peterson |
| 7,686,200 B2 | 3/2010 | Peterson |
| 7,950,559 B2 | 5/2011 | Peterson et al. |
| 8,066,736 B2 | 11/2011 | Peterson et al. |
| 8,074,857 B2 | 12/2011 | Peterson et al. |
| 8,100,939 B2 | 1/2012 | Peterson |
| 2002/0007184 A1 | 1/2002 | Ogilvie et al. |
| 2002/0019636 A1 | 2/2002 | Ogilvie et al. |
| 2002/0133181 A1 | 9/2002 | Tong |
| 2003/0028218 A1 | 2/2003 | Bauer |
| 2003/0139746 A1 | 7/2003 | Groiso |
| 2003/0233108 A1 | 12/2003 | Gellman et al. |
| 2003/0236550 A1 | 12/2003 | Peterson et al. |
| 2003/0236551 A1 | 12/2003 | Peterson |

(56) References Cited

U.S. PATENT DOCUMENTS

| | | |
|---|---|---|
| 2004/0059377 A1 | 3/2004 | Peterson et al. |
| 2004/0059378 A1 | 3/2004 | Peterson et al. |
| 2005/0033317 A1 | 2/2005 | Ables |
| 2005/0085857 A1 | 4/2005 | Peterson et al. |
| 2005/0149064 A1 | 7/2005 | Peterson et al. |
| 2005/0182444 A1 | 8/2005 | Peterson et al. |
| 2006/0135988 A1 | 6/2006 | Peterson |
| 2007/0232954 A1* | 10/2007 | Harris .................. A61B 10/02 600/564 |
| 2009/0093824 A1 | 4/2009 | Hasan et al. |
| 2012/0083831 A1 | 4/2012 | Peterson |
| 2012/0145765 A1 | 6/2012 | Peterson et al. |
| 2013/0267997 A1 | 10/2013 | Peterson et al. |
| 2015/0112369 A1 | 4/2015 | Peterson et al. |
| 2015/0127046 A1 | 5/2015 | Peterson |
| 2015/0305740 A1 | 10/2015 | Peterson et al. |

FOREIGN PATENT DOCUMENTS

| | | |
|---|---|---|
| FR | 2549544 A3 | 1/1985 |
| JP | 04-226642 A | 8/1992 |
| JP | 5-504892 | 7/1993 |
| JP | H6-233772 | 8/1994 |
| JP | 7124166 A | 5/1995 |
| JP | 2000217829 A | 8/2000 |
| JP | 2000-517197 | 12/2000 |
| WO | WO 97/18761 | 5/1997 |
| WO | WO 0057796 A1 | 10/2000 |
| WO | WO 0067644 A1 | 11/2000 |

OTHER PUBLICATIONS

Brochure: *Information Booklet for Auto Suture® Purse String Instrument*, Auto Suture Company, a division of United States Surgical Corporation, Norwalk, CT, 2 pgs., 1978.
Brochure: *La Sutura Perde il Filo*, Farmitalia Carlo Erba, 4 pgs., not dated.
*Evaluation of New Absorbable Lactomer Subcuticular Staple*, G.C. Zachmann, P.A. Foresman, T.J. Bill, D.J. Bentrem, G.T. Rodeheaver, R.F. Edlich, Journal of Applied Biomaterial, vol. 5, No. 3, pp. 221-116, 1994.
Suturtek Incorporated, http://www.suturtek.com/productInfo/,1/312007, p. 1 of 1, North Chelmsford, Massachusetts.
EP Communication dated Mar. 8, 2011 for EP Application No. 03761338.7 filed Jun. 25, 2003, 6 pages.
EP Communication dated Jan. 23, 2015 for EP Application No. 03761338.7 filed Jun. 25, 2003, 4 pages.
PCT Search Report dated Oct. 13, 2004 for PCT Application No. PCT/US03/20083 filed Jun. 25, 2003, 5 pages.
PCT Search Report and Written Opinion dated Jul. 1, 2015 for PCT Application No. PCT/US2015/025130 filed Apr. 9, 2015, 13 pages.
File history for U.S. Appl. No. 10/448,838, filed May 30, 2003. Inventors: James Peterson.
File history for U.S. Appl. No. 10/607,497, filed Jun. 25, 2003. Inventors: James Peterson et al.
File history for U.S. Appl. No. 10/603,397, filed Jun. 25, 2003. Inventors: James Peterson et al.
File history for U.S. Appl. No. 11/022,319, filed Dec. 23, 2004. Inventors: James Peterson et al.
File history for U.S. Appl. No. 11/003,145, filed Dec. 3, 2004. Inventors: James Peterson et al.
File history for U.S. Appl. No. 11/097,085, filed Apr. 1, 2005. Inventors: James Peterson et al.
File history for U.S. Appl. No. 13/314,978, filed Dec. 8, 2011. Inventors: James Peterson et al.
File history for U.S. Appl. No. 13/796,798, filed Mar. 12, 2013. Inventors: James Peterson et al.
File history for U.S. Appl. No. 11/316,322, filed Dec. 22, 2005. Inventor: James Peterson.
File history for U.S. Appl. No. 11/487,951, filed Jul. 17, 2006. Inventor: James Peterson.
File history for U.S. Appl. No. 13/324,680, filed Dec. 13, 2011. Inventor: James Peterson.
File history for U.S. Appl. No. 14/555,004, filed Nov. 26, 014. Inventor: James Peterson.
File history for U.S. Appl. No. 14/471,519, filed Aug. 28, 2014. Inventors: James Peterson et al.

\* cited by examiner

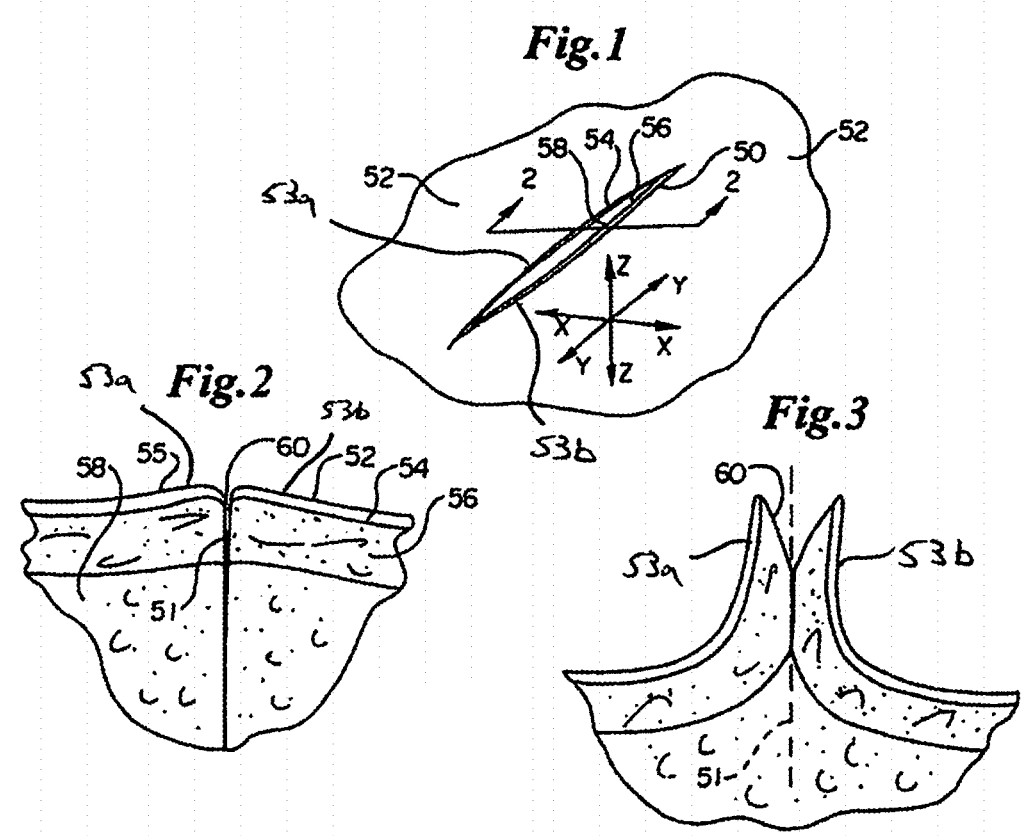

SURGICAL FASTENING INSTRUMENT

FIELD OF THE INVENTION

The present invention is generally directed to the field of wound closure. More specifically, the present invention is directed to an apparatus and related methods of positioning and retaining tissue so as to assure fastener placement within subcuticular dermal tissue and avoid or reduce the potential risk for inadvertent piercing and percutaneous placement of the surgical fastener through the external skin surface.

BACKGROUND OF THE INVENTION

Throughout history, sutures have been utilized to capture and retain tissue in approximation during a wound healing period. More recently, metal staples and staplers have been developed to speed the closure process. While both suturing and stapling are effective, they are each prone to infection, unsightly scarring and can require subsequent medical follow ups for removal of the staple by a medical professional.

In a desire to improve upon the existing techniques for wound closure, an approach to wound closure through the insertion of a subcuticular bioabsorbable fastener in dermal tissue is described in U.S. Pat. Nos. 6,726,705, 7,112,214, 7,547,315, 7,686,200, 7,950,559, 8,066,736 and 8,074,857, U.S. Patent Publication Nos. 2012/0145765 and 2013/0267997 to Peterson et al. and U.S. patent application Ser. No. 14/262,071 to Peterson et al., all of which are herein incorporated by reference in their entirety. These devices and methods have been developed and/or commercialized as the INSORB® line of surgical staplers available from Incisive Surgical, Inc. of Plymouth, Minn. By using a subcuticular dermal insertion and fastening approach as taught by the various Peterson et al. references, visible scarring is minimized and incidences of infection are significantly reduced.

In order to have optimal wound closure and healing, it is desired to avoid any piercing of the epidermis and the unintentional placement of the surgical fastener through the external skin surface (percutaneous). This external placement of fasteners is difficult for the practitioner to avoid and requires that that the fastener must be removed. If detected in the operating suite, the removal of the fastener will delay and interrupt the wound closure procedure. If the externally placed fastener is not detected at the time of surgery, it typically requires corrective intervention in a clinician's office resulting in an additional patient follow-up visit. This is a frequent cause of user frustration and increases the cost and inconvenience for both the patient and clinician. As such, it would be advantageous to further improve upon the devices and methods as taught by Peterson et al. so as to reduce or eliminate the risk of fasteners being misplaced through the external skin surface, improve the clinical outcome and clinician and patient experience.

SUMMARY OF THE INVENTION

The present application is directed to a surgical fastening apparatus and related methods for fastening skin tissue so as to avoid piercing the epidermis when placing surgical fasteners within a dermal layer on opposed sides of a skin wound. The apparatus includes a device body having a head portion for positioning between first and second sides of the wound, wherein the head portion includes a lower deflector shelf that physically prevents an external skin surface and/or a wound edge from entering a tissue capture area through which a penetrator assembly and fastener are advanced into the dermal layer. By physically blocking the external skin surface and/or wound edge from placement within the capture area, the potential for inadvertent piercing and percutaneous placement of the surgical fastener entering though the external skin surface is avoided.

In one aspect of the present invention, a skin fastening device can comprise a device body including a head portion, a pair of laterally opposed approximation arms and an actuator assembly. The actuator assembly can direct the laterally opposed approximation arms into proximity with the head portion for positioning and retaining skin tissue. The head portion can define a capture area through which a penetrator assembly and fastener are advanced into and through retained dermal skin tissue. The head portion can comprise a lower deflector shelf positioned at least partially below the capture area wherein the lower deflector shelf physically prevents an external skin surface and/or tissue edge of the retained skin tissue from entering the capture area. As the penetrator assembly and the fastener traverse the capture area, only a dermal or subcuticular surface of the retained skin tissue can be pierced such that there is no piercing of the epidermal surface or the wound edge. In some embodiments, the head portion can comprise a distal receiver, a proximal wall and an upper connecting wall with the capture area defined therebetween. The lower deflector shelf can project forward from a lowermost point of the proximal wall. In some embodiments, the distal receiver can comprise a pair of lateral downward lobes extending down from the upper connecting wall and defining a receiver gap between the lateral downward lobes. The penetrator assembly and fastener can be advanced through the receiver gap, whereby the penetrator assembly can be retracted through the receiver gap as the fastener remains positioned within the retained dermal or subcuticular tissue.

In another aspect of the present invention, a method for skin fastening can comprise positioning a head portion of a fastening device within a wound and between opposed sides of tissue. The method can further comprise manipulating a pair of laterally opposed approximation arms into proximity with opposed sides of the head portion so as to place the opposed sides of tissue into contact with the head portion. The method can further comprise contacting an inner skin surface on each of the opposed sides of tissue with a deflector shelf on the head portion so as to prevent an external skin surface and/or skin edge from entering a capture area defined on the head portion. The method can further comprise advancing a fastener through the capture area and into the opposed sides of dermal tissue. In some embodiments, the method can comprise advancing a fastener to a distal receiver on the head portion. The distal receiver can comprise a pair of lateral downward facing lobes defining a receiver gap such that the fastener can be advanced into the receiver gap. In some embodiments, the method can further comprise withdrawing a penetrator assembly from the receiver gap, whereby the fastener remains positioned within the opposed sides of dermal tissue. In some embodiments, the method can further comprise draping the opposed sides of tissue over a visual indicator that is present on each side of the head portion. In some embodiments, the head portion can be oriented generally parallel to a skin surface while yet in other embodiments, the head portion can be oriented in a generally perpendicular or oblique position relative to the skin surface. In some embodiments, the wound can comprise a linear skin incision or linear skin wound while in other embodiments, the wound can comprise a generally circular skin port.

The above summary of the various representative embodiments of the invention is not intended to describe each illustrated embodiment or every implementation of the invention. Rather, the embodiments are chosen and described so that others skilled in the art can appreciate and understand the principles and practices of the invention.

BRIEF DESCRIPTION OF THE DRAWINGS

The invention can be more completely understood in consideration of the following detailed description of various embodiments of the invention in connection with the accompanying drawings, in which:

FIG. 1 is a top, perspective view of a skin tissue opening.

FIG. 2 is a section view of the skin tissue opening of FIG. 1 taken at line 2-2 of FIG. 1.

FIG. 3 is a section view of the skin tissue opening of FIG. 1 having opposing tissue sides arranged in an approximated, everted disposition.

Figure 4:
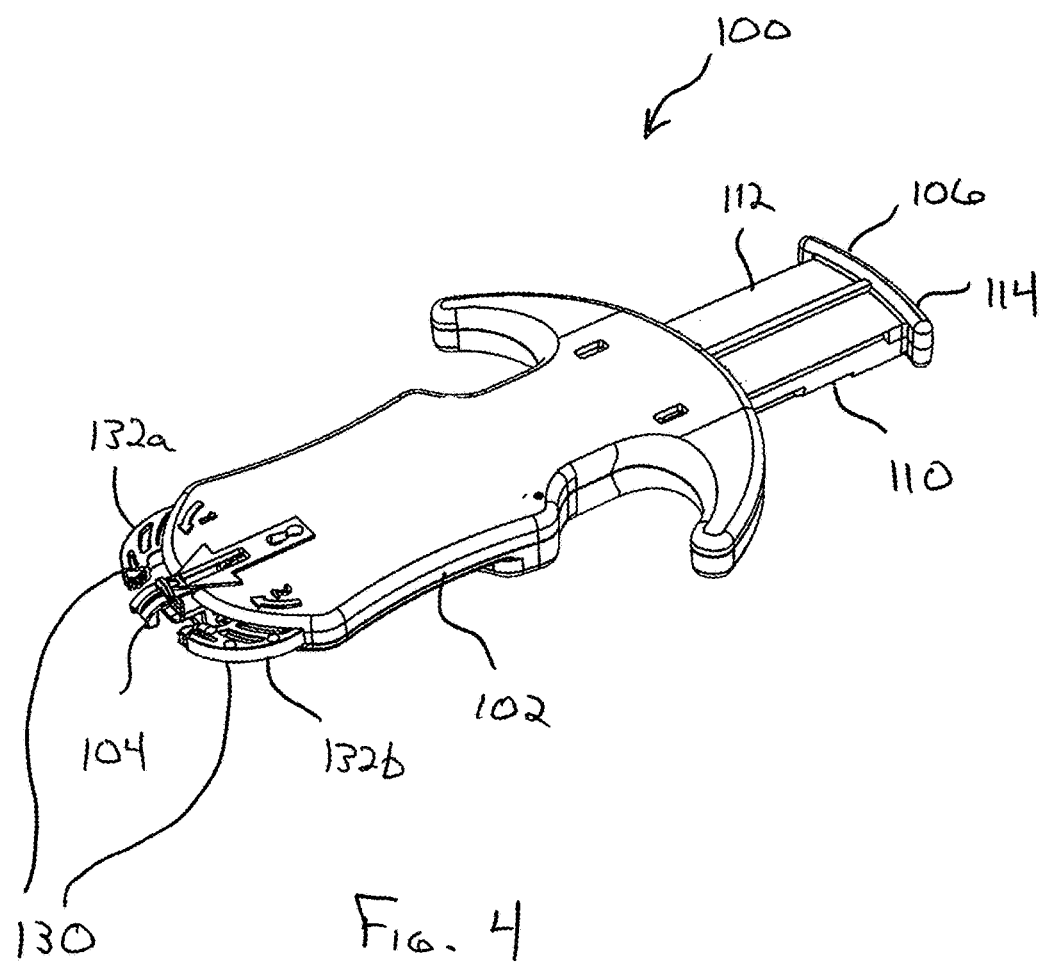
FIG. 4 is a top, perspective view of a skin fastening device according to a representative embodiment of the present invention.

While the invention is amenable to various modifications and alternative forms, specifics thereof have been shown by way of example in the drawings and will be described in detail. It should be understood, however, that the intention is not to limit the invention to the particular embodiments as described. On the contrary, the intention is to cover all modifications, equivalents, and alternatives falling within the spirit and scope of the invention as defined by the appended claims.

DETAILED DESCRIPTION OF THE DRAWINGS

In FIGS. 1-3 there is shown a depiction of a typical opening 50 in the surface of skin 52 having a pair of wound sides 53a, 53b, such as may be made, for example, by a surgical incision or a wound. As illustrated in FIG. 1, for purposes of describing the present invention, opening 50 may be described as having a length or longitudinal orientation parallel to the y-y axis, a width orientation parallel to the x-x axis, and a depth orientation parallel to the z-z axis. The x-y-z axis for purposes of the present invention is defined with respect to an external tissue surface, which in the case of skin 52 is the outer surface. References to a vertical and horizontal planar orientation in connection with the present invention are made with respect to the external tissue surface at the site of the opening in question. The vertical inner surfaces 60 formed by each side of the opening 50 can be visualized as meeting along a generally vertical interface 51. It will be understood that in the case of an opening that extends over a curved tissue surface, the corresponding horizontal and vertical surfaces associated with the opening will be defined with respect to such curved tissue surface. It also will be understood that the vertical interface 51 may be vertical in only one orientation with respect to the tissue surface, such as in the case when an angled incision has formed the opening 50. Opening 50 can be under high tension based on its size or location on the body. For example, opening 50 can include laparoscopic or circular skin ports or be the result of tissue excision or irregular incisions/lacerations.

As is best illustrated in the sectional views of FIGS. 2 and 3, human skin 52 generally has three discrete layers. These layers comprise an epidermal layer 54 of mostly non-living tissue having an exterior surface 55, a dermal layer 56 of mostly living tissue, and a subcutaneous tissue layer 58. Although the preferred embodiment of the present invention will be described with respect to human skin tissue 52, it will be understood that the present invention is applicable to closure of openings in other types of tissue having generally defined surfaces, such as fascia, membranes organs, vessels, vasculature, vascular pedicles, skin grafts, bladder and other biocompatible materials with generally defined surfaces such as artificial skin, artificial membranes and synthetic mesh.

It has long been known that the most rapid healing of a skin opening with a minimum of scarring occurs when the inner surfaces 60 of the living dermal layer 56 at each side of the vertical interface 51 of skin opening 50 are brought together and held in close contact in what is referred to as an everted position as is shown in exaggerated fashion in FIG. 3. To the extent that the primarily non-living material of epidermal layer 54 can be excluded from the healing opening, the rapidity and level of scar tissue formed during the healing process will be improved. Referring now to FIG. 4, a representative embodiment of a skin fastening device 100 for grasping and fastening skin tissue is illustrated. Generally, skin fastening device 100 and it various component parts as will be further described can be constructed of materials suitable for use in a surgical environment including metals such as, stainless steel or various polymers.

Generally, skin fastening device 100 comprises a device body 102 having a fastening end 104 and an actuation end 106. Skin fastening device 100 can substantially resemble the skin fastening device described in U.S. patent application Ser. No. 14/262,071 filed Apr. 25, 2014 and entitled "METHOD AND APPARATUS FOR WOUND CLOSURE WITH SEQUENTIAL TISSUE POSITIONING AND RETENTION", the disclosure of which is hereby incorporated by reference in its entirety, with the further inclusion of enhancements proximate the fastening end 104 to enhance performance, ease of use, speed and safety.

Figure 5:
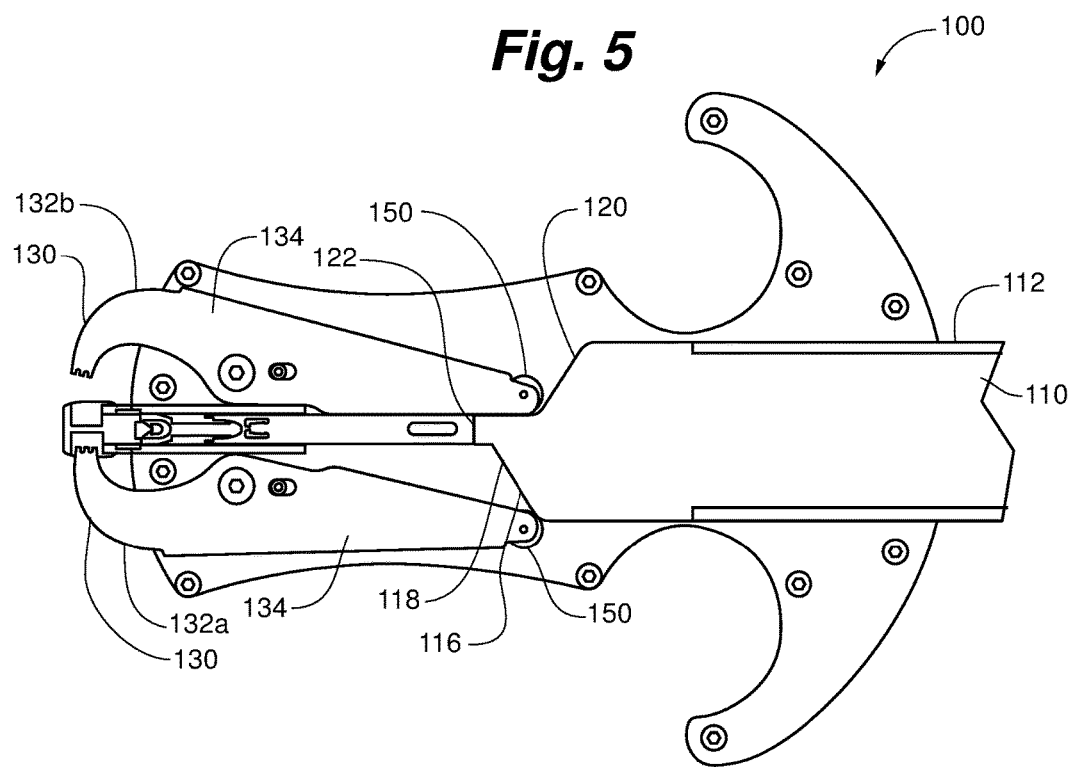
FIG. 5 is a bottom, partially hidden view of the skin fastening device of FIG. 4.
Figure 7:
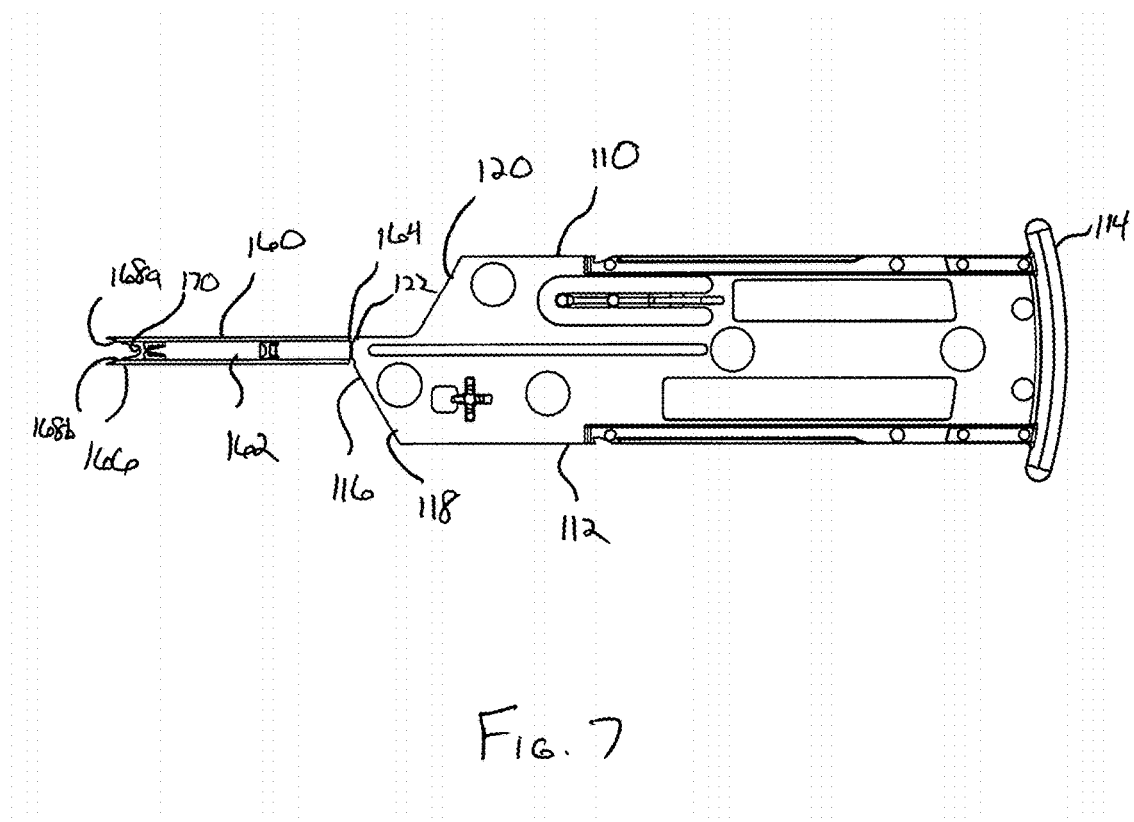
FIG. 7 is a top view of an actuation assembly and a penetrator assembly of the skin fastening device of FIG. 4.

Referring now to FIGS. 4, 5 and 7, skin fastening device 100 generally comprises an actuator assembly 110 that is mounted within the device body 102 for slidable advancement and retraction. Generally, actuator assembly 110 includes an actuator body 112 having a grasping end 114 and an actuation end 116 that remains contained within the device body 102. The actuation end 116 can comprise a first angled actuation surface 118, a second angled actuation surface 120 and an actuation projection 122.

Figure 6:
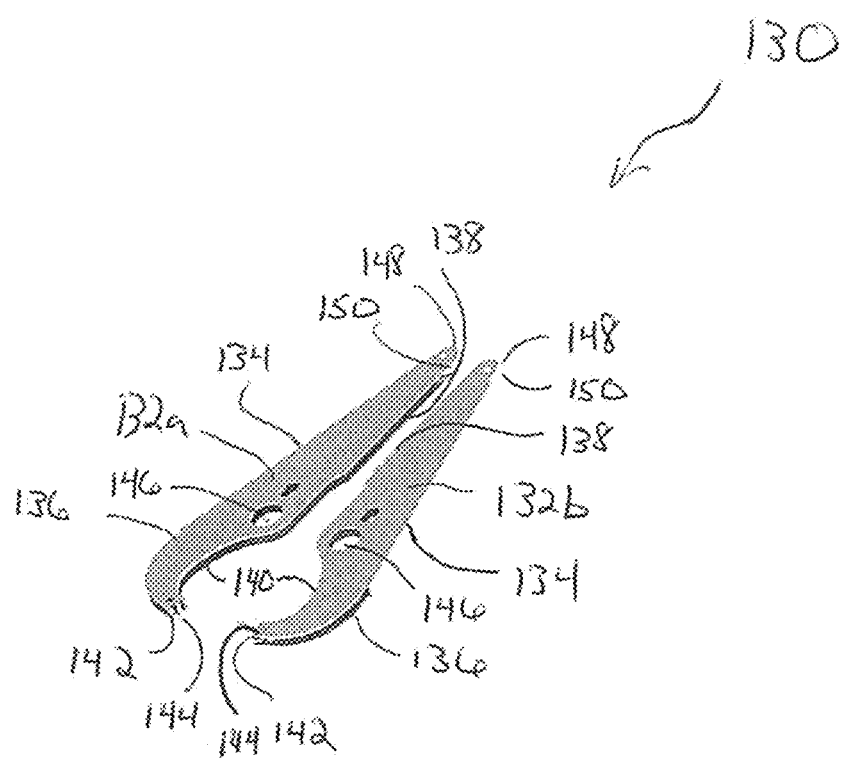
FIG. 6 is a perspective view of a sequential retention assembly of the skin fastening device of FIG. 4.

As seen in FIGS. 4-6, skin fastening device 100 can further comprise a sequential retention assembly 130. Sequential retention assembly 130 generally comprises first and second approximation arms 132a, 132b that are essentially mirror images of one another. Each of the first and second approximation arms 132a, 132b include an arm body 134 defined by an exterior wall 136, an interior engagement wall 138 and a retention wall 140. Exterior wall 136 and retention wall 140 are coupled at a grasping wall 142. Each grasping wall 142 can comprise one or more jaws or teeth 144. Each arm body 134 has a generally flat profile and includes an arm mounting aperture 146. In some embodiments, exterior wall 136 and interior engagement wall 138 can define a rounded engagement portion 148. In some embodiments, rounded engagement portion 148 can further include a rotatable engagement member 150. First and second approximation arms 132a, 132b can be fabricated of a rigid, nonflexible material to as to promote consistent retention of skin tissue with respect to the fastening end 104 of the skin fastening device 100. In some embodiments, the first and second approximation arms 132a, 132b can be fabricated from stainless steel or other durable, non-corroding metals or metal alloys.

Referring again to FIG. 7, skin fastening device 100 can further include a penetrator assembly 160. Generally penetrator assembly 160 can comprise a slidable body 162 having a driving end 164 and a fastening end 166. At the fastening end 166, the slidable body 162 can comprise a pair of penetrator members 168a, 168b that are operably connected via an arcuate rear wall 170.

Figure 8:
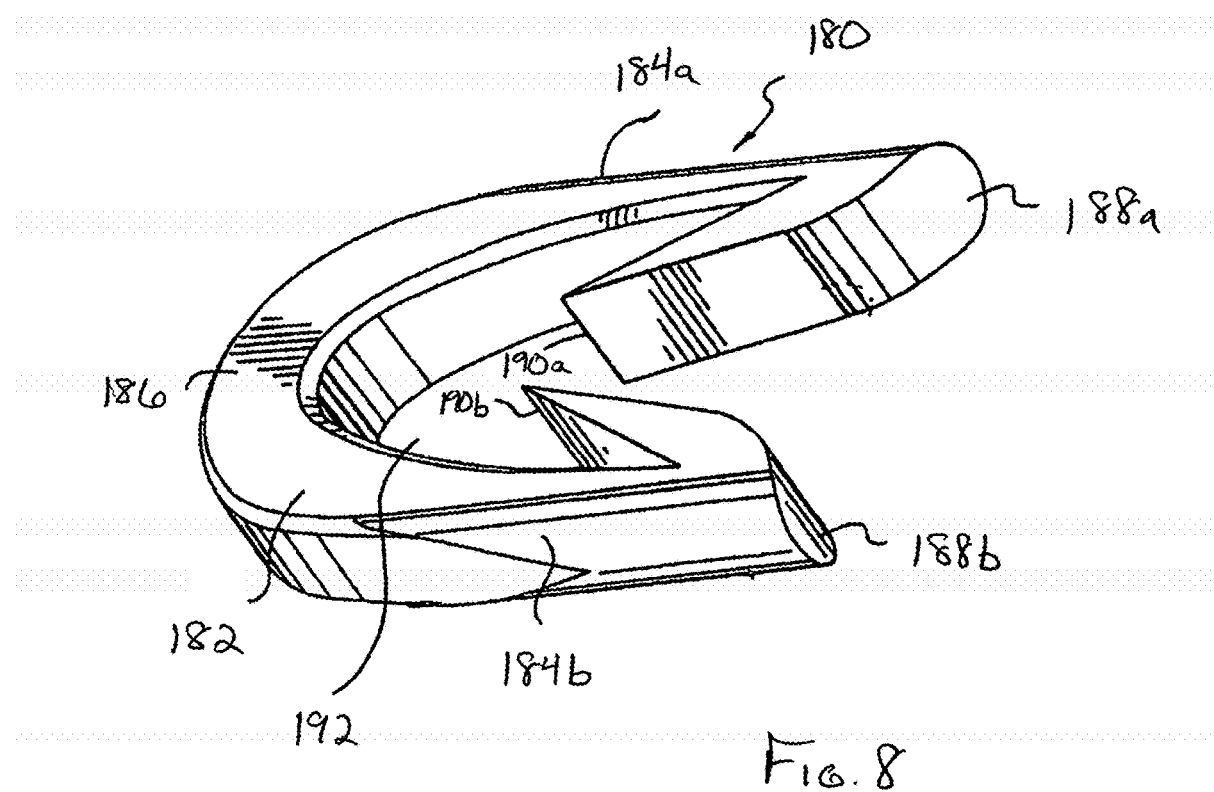
FIG. 8 is a perspective view of a skin fastener of the skin fastening device of FIG. 4.
Figure 9:
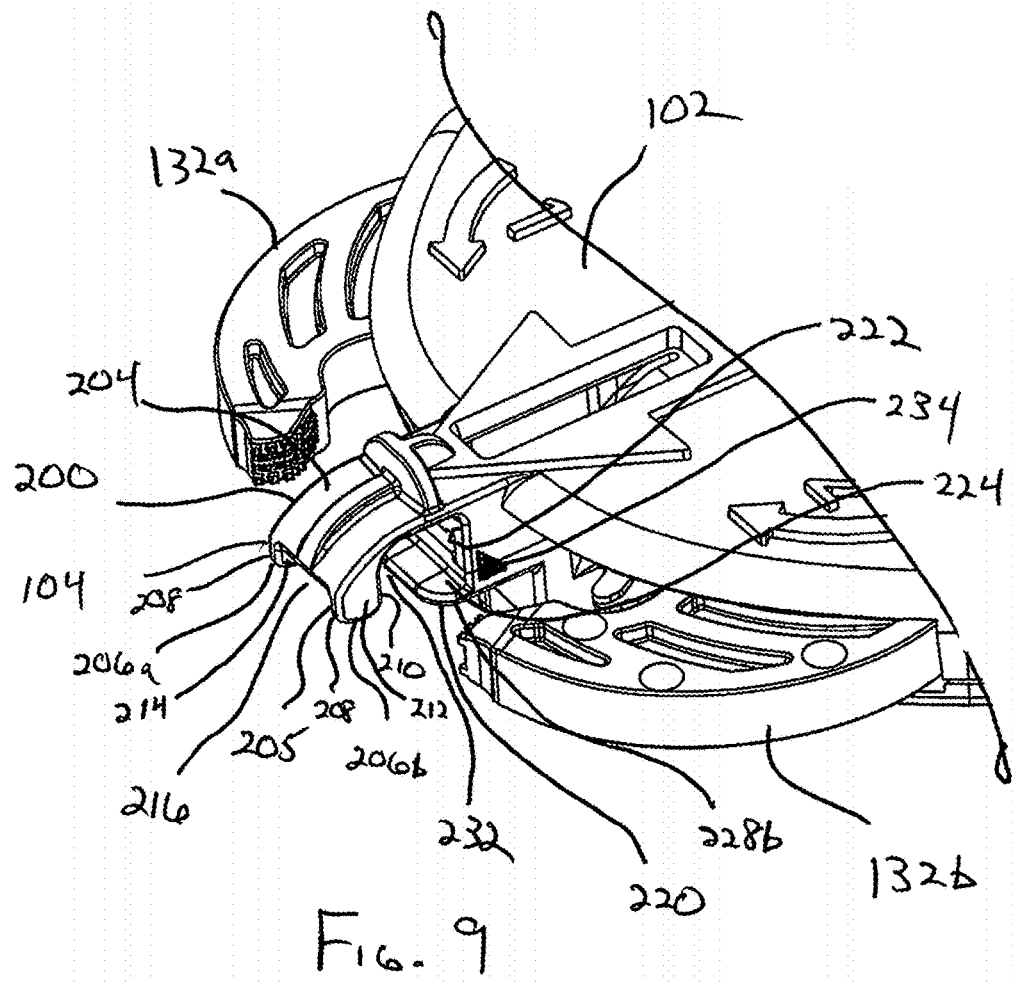
FIG. 9 is a top, detailed perspective view of a fastening end of the skin fastening device of FIG. 4.
Figure 10:
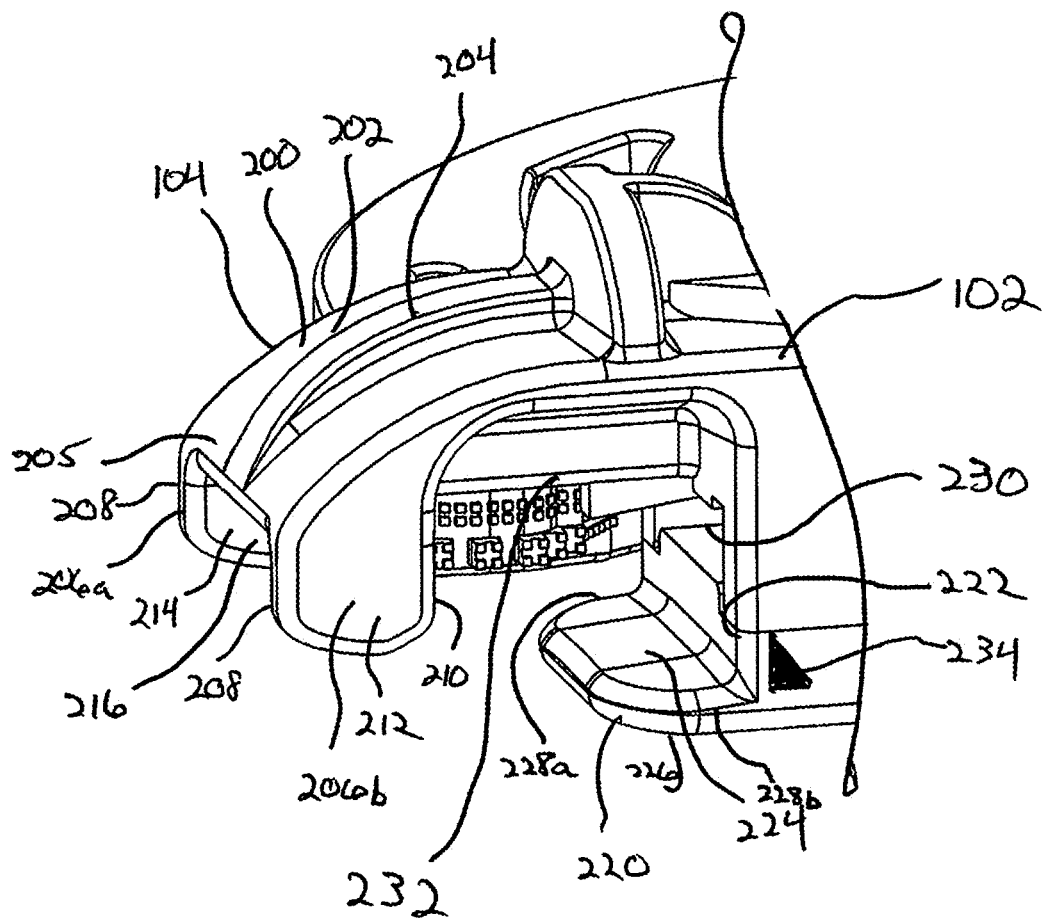
FIG. 10 is a side, perspective view of the fastening end of FIG. 9.
Figure 11:
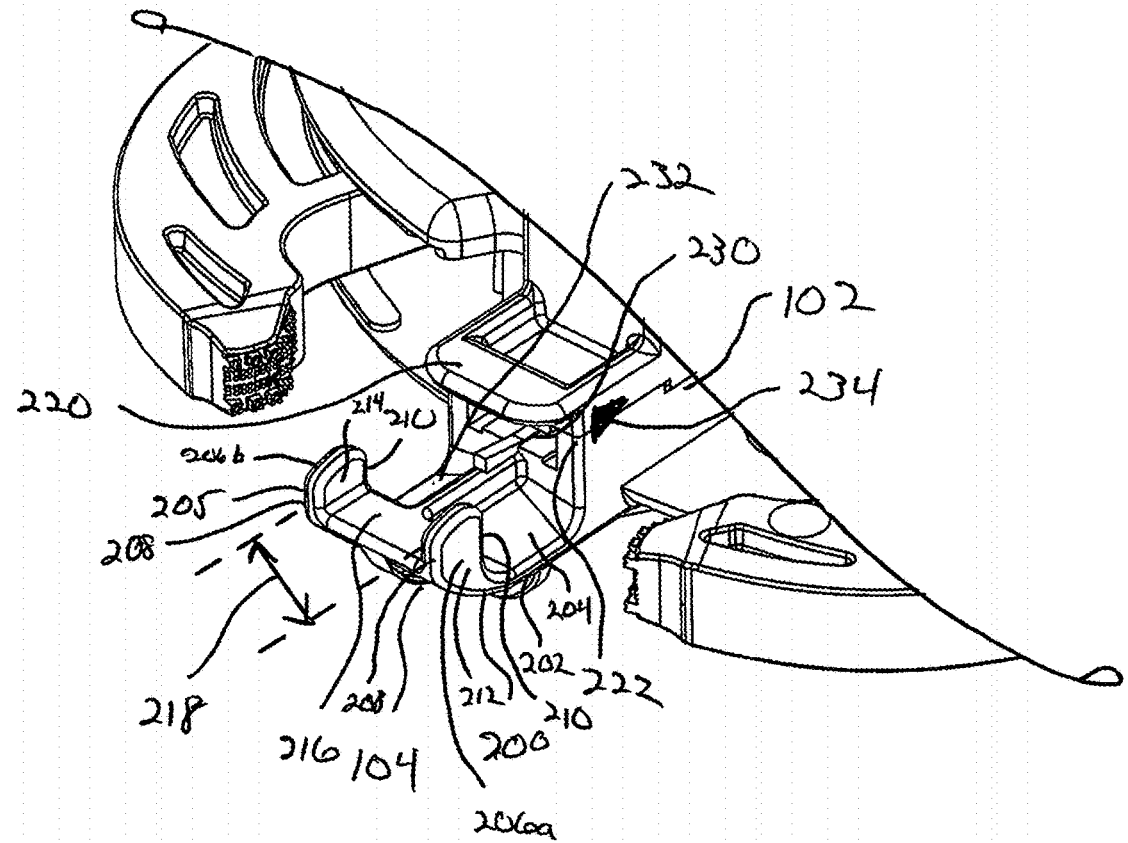
FIG. 11 is a bottom, perspective view of the fastening end of FIG. 9.
Figure 12:
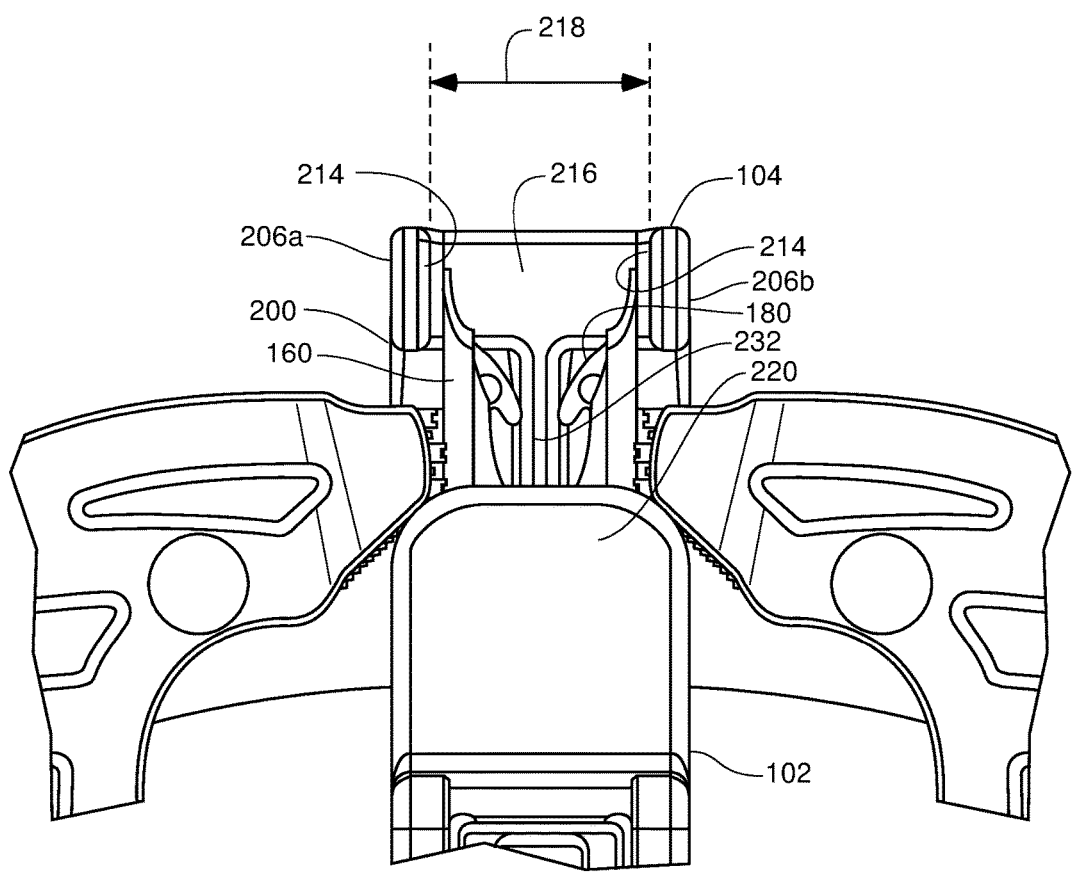
FIG. 12 is a bottom view of the fastening end of FIG. 9.

As illustrated in FIG. 8, skin fastening device 100 generally includes one or more bioabsorbable fasteners or staples 180 such as, for example, those illustrated and described in U.S. Pat. Nos. 7,112,214 and 8,066,736, both of which are commercially available from the assignee of the present application, Incisive Surgical of Plymouth, Minn. Fastener 180 generally comprises a fastener body 182 having a pair of staple arms 184a, 184b that are connected with an arcuate backspan 186. Each staple arm 184a, 184b can have a rounded tip 188a, 188b, from which a hook portion 190a, 190b can project inwardly so as to define a fastener capture area 192.

With reference to FIGS. 4, 5 and 9-12, fastening end 104 of the skin fastening device 100 generally comprises a head portion 200. Head portion 200 generally includes a head body 202 that projects distally from the device body 102. The head body 202 generally includes an upper connecting wall 204 extends distally of the device body 102 and terminates in distal receiver 205. The distal receiver 205 generally comprises a pair of lateral lobes 206a, 206b. Each of the lateral lobes 206a, 206b includes a distal lobe wall 208, a proximal lobe wall 210, an exterior lobe wall 212 and an interior lobe wall 214. The lateral lobes 206a, 206b define a receiver gap 216 between the corresponding interior lobe walls 214. The receiver gap 216 has a gap width 218 that is selected so as to be slightly oversized with respect to the width of the penetrator assembly 160, whereby the penetrator members 168a, 168 can be advanced into the receiver gap 216.

Referring again to FIGS. 9-12, fastening end 104 can further comprise a deflector shelf 220 that extends forward from a proximal body wall 222 of the device body 102. Deflector shelf 220 generally comprises a top shelf surface 224, a bottom shelf surface 226 and a pair of shelf side surface 228a, 228b. Generally, the deflector shelf 220 extends from a lowermost portion of the proximal body wall 222 such that deflector shelf 220 resides below a penetrator opening 230 defined in the proximal body wall 222. Generally, the deflector shelf 220, the proximal body wall 222, the upper connecting wall 204 and the distal receiver 205 cooperatively define a tissue capture area 232. Fastening end 104 can further comprise a visual marker 234 positioned on body side walls 236a, 236b in proximity to the proximal body wall 222 on the device body 102. Visual marker 234 can provide further visual reference to a medical professional with respect to proper positioning of the wound sides 53a, 53b relative to the head portion 200, i.e. covering of the visual marker 234 with wound sides 53a, 53b such that the visual marker 234 is no longer visible.

Figure 13:
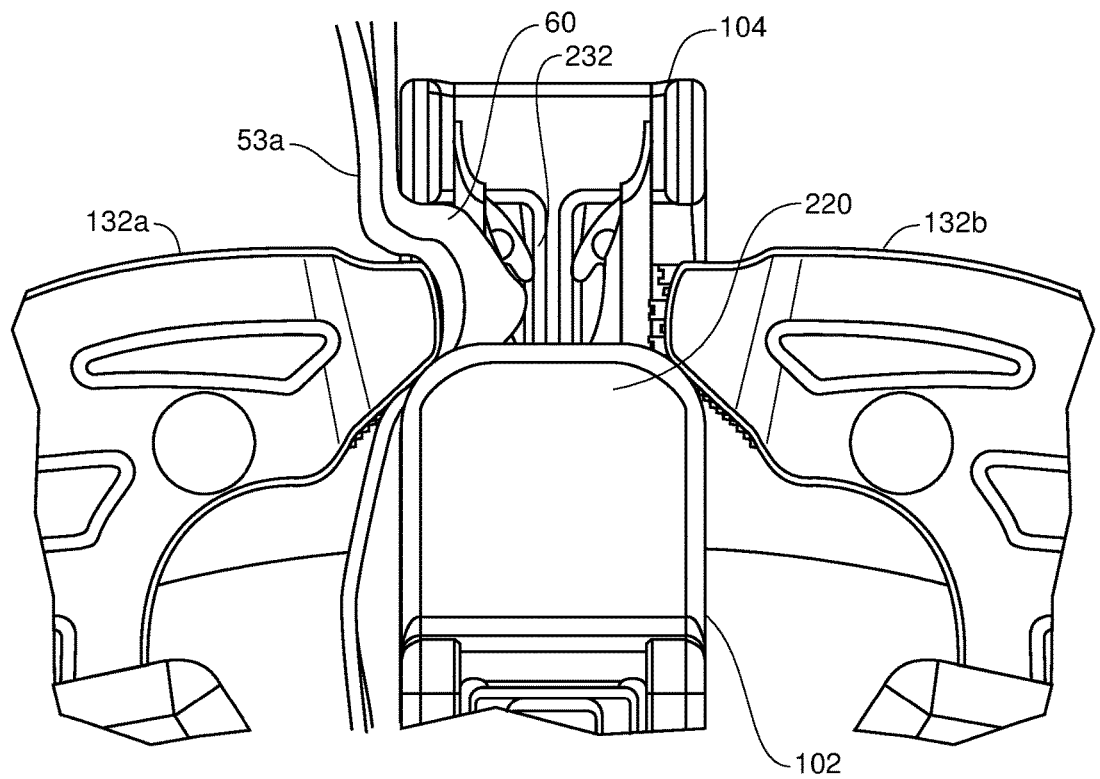
FIG. 13 is a bottom view of the fastening end of FIG. 9 retaining a wound side.
Figure 14:
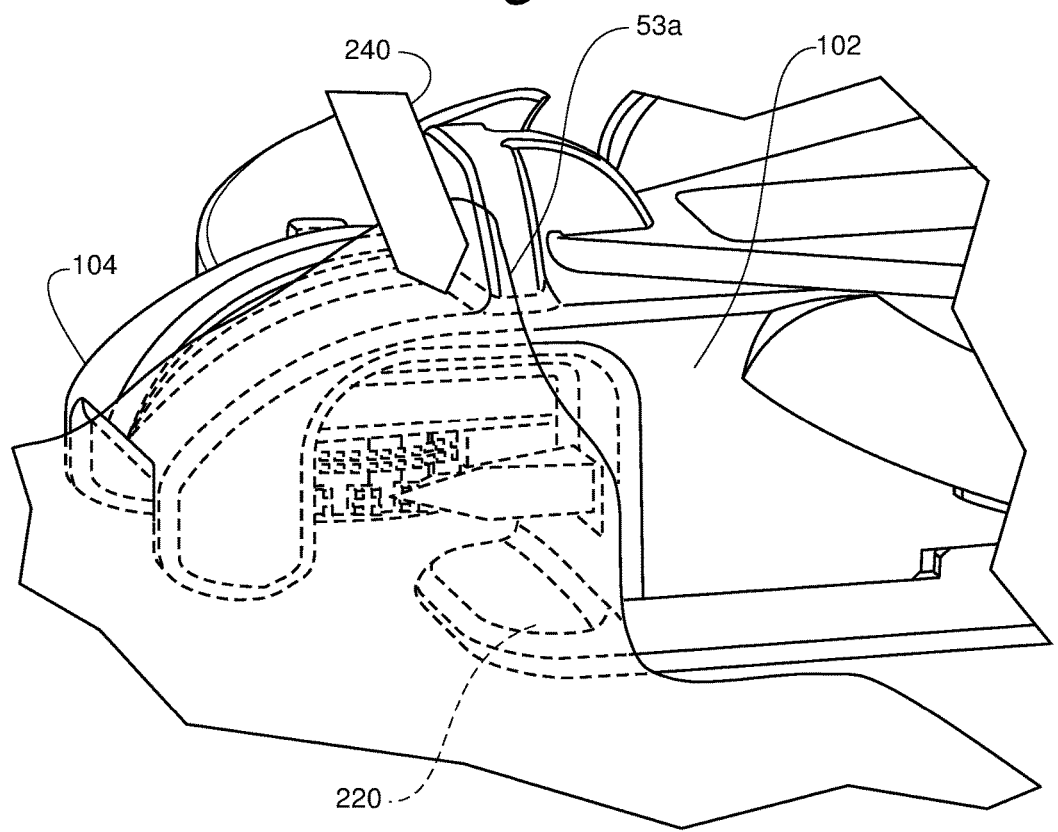
FIG. 14 is a side, perspective, partially hidden view of the fastening end of FIG. 9 with a wound side positioned against a deflector shelf.

With reference to the operation of skin fastening device 100, the device body 102 can be oriented such that the head body 202 is positioned within skin opening 50. Using the grasping end 114, the user then begins to advance the actuator body 112 into the device body 102. As the actuator body 112 slides into the device body 102, the actuation end 116 is directed toward the fastening end 104. As the actuation end 116 is advanced, the first angled actuation surface 118, followed by the second angled actuation surface 120 sequentially come into contact with the corresponding rotatable engagement members 150, thereby causing the first approximation arm 132a followed by the second approximation arm 132b to begin to rotate about a projecting member over which each of the arm mounting apertures 146 are individually mounted. As the advancement of the actuator body 112 continues, the rotatable engagement members 150 of the first and second approximation arms 132a, 132b move along the first angled actuation surface 118 and second angle actuation surface 120 respectively such that the first and second approximation arms 132a, 132b continue their rotation, thereby resulting in each grasping wall 142 and the corresponding teeth 144 to approach and grab the exterior surface of the wound sides 53a, 53b on each side of the skin opening 50. As the first and second approximation arms 132a, 132b continues their rotation, the grasping wall 142 and teeth 144 of the first and second approximation arms 132a, 132b position and force the inner surface 60 of the wound sides 53a, 53b into the tissue capture area 232 as shown in FIG. 13 with respect to wound side 53a. As illustrated in FIG. 14, a medical professional can utilize an instrument such as, for example, a forceps 240 to assist with positioning the wound sides 53a, 53b prior to capture by the first and second approximation arms 132a, 132b.

Figure 15:
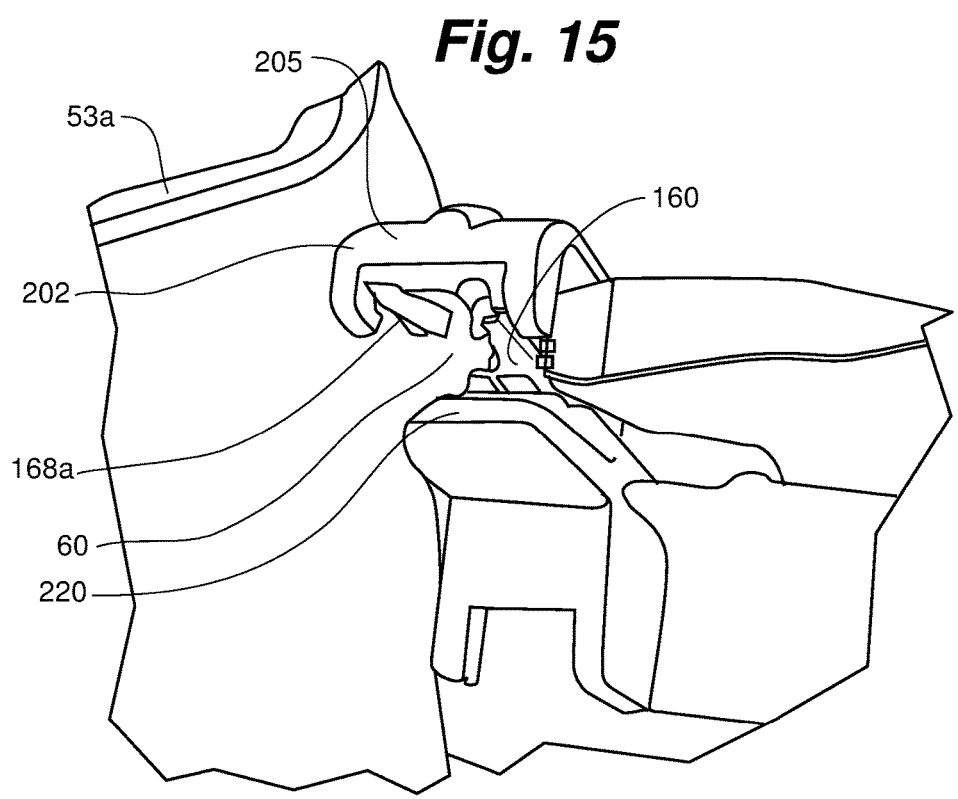
FIG. 15 is a perspective, end view of the fastening end of FIG. 9 with a penetrator assembly piercing a wound side.

With reference to FIG. 15, the capture of wound side 53a (wound side 53b not shown for purposes of clarity though understood to interact similarly) relative to the tissue capture area 232 causes the wounds sides 53a to come into contact with the shelf side surfaces 228a of the deflector shelf 220. The deflector shelf 220 acts as a physical impediment so as to limit the amount of the wounds side 53a that can enter the tissue capture area 232. By causing the wound side 53a to conform to the deflector shelf 220, the medical professional can ensure that only the dermal layer 56 and subcuticular layer 58 are presented in the pathway of the penetrator member 168a and that that the epidermal layer 54 is not presented for piercing by the penetrator member 168a.

As the actuation end 116 continues toward the fastening end 104, the actuation projection 122 causes the penetrator assembly 160 to be directed toward the penetrator opening 230. As the penetrator assembly 160 is advanced, a fastener 180 is collected between the penetrator members 168a, 168b and the arcuate rear wall 170. Continued advancement of the actuation end 116 causes the penetrator assembly 160, now carrying the fastener 180, through the penetrator opening 230 and into the inner surface 60 of the wound sides 53a, 53b. As the penetrator assembly 160 traverses the tissue capture area 232 from the proximal body wall 222 toward the distal receiver 205, the staple arms 184a, 184b are carried through the pierced tissue openings created by the penetrator members 168a, 168b. The penetrator members 168a, 168b are advanced toward the proximal lobe walls 210, whereby the penetrator members 168a, 168b traverse the receiver gap 216. As the rounded tips 188a, 188b on the fasteners 180 enter the receiver gap 216, the wound sides 53a, 53b are retained within the tissue capture area 232 such that the rounded tips 188a, 118b exit the pierced tissue openings. The actuator body 112 can then be retracted from device body 102 such that the penetrator assembly 160 is withdrawn from the receiver gap 216, is pulled through the tissue capture area 232 and into the penetrator opening 230, whereby the fastener 180 remains within the inner surface 60 of the wound sides 53a, 53b so as to retain the wound sides 53a, 53b in approximation for healing. The user can then pull the fastening end 104 rearward without withdrawing the head portion 200 from the wound from the opening 50 to place the next fastener 180 in the event that multiple fasteners 180 are necessary to fully close the wound 50. Using the skin fastening device 100, the device body 102 can be manipulated so as to deliver fasteners 180 in parallel, perpendicular or oblique orientations relative to an exterior surface 55 of skin 52.

Although specific examples have been illustrated and described herein, it will be appreciated by those of ordinary skill in the art that the present application is intended to cover adaptations or variations thereof of the presently disclosed invention. Therefore, it will be understood that the scope of the present invention is defined by the attached claims and their legal equivalents.

The invention claimed is:

1. A skin fastening device, comprising:
a device body having a head portion and a pair of opposed approximation arms located on opposed lateral sides of the head portion, the device body further including an actuator assembly for manipulating the opposed approximation arms into proximity with the head portion and to advance a fastener distally within the head portion,
wherein the head portion defines a capture area between a distal receiver, a proximal wall, a deflector shelf and an upper connecting wall, and
a penetrator assembly configured for advancement along a path between the proximal wall and the distal receiver and through the capture area,
wherein the deflector shelf extends from the proximal wall and toward the distal receiver such that the deflector shelf resides below the capture area and the path of advancement of the penetrator assembly,
the deflector shelf configured to contact an internal surface of skin tissue, whereby an external surface of skin tissue and wound edge is prevented from entering into the capture area.

2. The skin fastening device of claim 1, wherein the deflector shelf extends forward from a lowermost point of the proximal wall.

3. The skin fastening device of claim 1, wherein the penetrator assembly is advanced through the capture area at the direction of the actuator assembly, the penetrator assembly carrying the fastener from the proximal wall toward the distal receiver.

4. The skin fastening device of claim 1, wherein the distal receiver comprises a pair of lateral lobes extending downward from the distal receiver.

5. The skin fastening device of claim 4, wherein the lateral downward lobes define a receiver gap between them, wherein the fastener is advanced into the receiver gap.

6. The skin fastening device of claim 1, wherein the proximal wall defines a pair of opposed lateral walls, and wherein each lateral wall includes a visual indicator, wherein placement of skin tissue over each visual indicator provides indication that skin edges and external surfaces are not within the penetrator path of advancement of the penetrator assembly and the opposed approximation arms can then be manipulated with the actuator assembly.

7. A method for skin fastening, comprising:
positioning a head portion of a fastening device within a wound between opposed sides of internal dermal tissue;
manipulating a pair of opposed approximation arms on the fastening device into proximity with the head portion such that the opposed sides of the skin wound are directed into contact with the head portion;
contacting an inner skin surface on each of the opposed sides of the skin wound with a deflector shelf on the head potion, whereby the deflector shelf is configured to reside below a path of travel of a penetrator assembly such that the deflector shelf physically blocks an external skin surface on each of the opposed sides of the skin wound from entering a capture area defined in the head portion; and
advancing a fastener along the path of travel, through the capture area and into the opposed sides of internal dermal tissue.

8. The method of claim 7, wherein advancing the fastener through the capture area further comprises:
advancing the fastener to a distal receiver of the head portion.

9. The method of claim 8, wherein the distal receiver comprises a pair of downward facing lobes defining a receiver gap, and wherein advancing the fastener to the distal receiver of the head portion, further comprises:
advancing the fastener into the receiver gap.

10. The method of claim 7, wherein the head portion comprises a proximal wall from which the deflector shelf extends into the capture area, the proximal wall having a pair of opposed lateral walls, the method further comprising:
draping the opposed sides of the skin wound so as to cover a visual indicator on each of the opposed lateral walls.

11. The method of claim 7, wherein the skin wound comprises a linear skin incision or linear skin laceration.

12. The method of claim 7, wherein the skin wound comprises a circular skin port.

13. The method of claim 7, wherein positioning a head portion of a fastening device within a wound between opposed sides of internal dermal tissue, further comprises:
orienting the head portion so as to be generally parallel to a skin surface in which the skin wound resides.

14. The method of claim 7, wherein positioning the head portion of a fastening device within a wound between opposed sides of internal dermal tissue, further comprises:
orienting the head portion so as to be generally perpendicular to a skin surface in which the skin wound resides.

15. The method of claim 7, wherein positioning the head portion of a fastening device within a wound between opposed sides of internal dermal tissue, further comprises:
orienting the head portion so as to be positioned obliquely relative to a skin surface in which the skin wound resides.

* * * * *

UNITED STATES PATENT AND TRADEMARK OFFICE
CERTIFICATE OF CORRECTION

PATENT NO. : 10,085,747 B2
APPLICATION NO. : 14/851308
DATED : October 2, 2018
INVENTOR(S) : Peterson et al.

Page 1 of 1

It is certified that error appears in the above-identified patent and that said Letters Patent is hereby corrected as shown below:

In the Claims

Column 8, Line 6, delete "penetrator"

Column 8, Line 19, delete "potion" and insert --portion--

Signed and Sealed this
Eighth Day of January, 2019

Andrei Iancu
*Director of the United States Patent and Trademark Office*